US010646623B2

United States Patent
Li et al.

(10) Patent No.: US 10,646,623 B2
(45) Date of Patent: *May 12, 2020

(54) IMPLANTABLE MEDICAL DEVICE

(71) Applicant: DePuy International Limited, Leeds (GB)

(72) Inventors: Yufu Li, Bridgewater, NJ (US); Deborah Schachter, Edison, NJ (US); Raymond S. Shissias, Iselin, NJ (US); Sandra Wechsler, Wettingen (CH)

(73) Assignee: DePuy International Limited, Leeds, West Yorkshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/828,984

(22) Filed: Dec. 1, 2017

(65) Prior Publication Data

US 2018/0140751 A1 May 24, 2018

Related U.S. Application Data

(63) Continuation of application No. 13/124,532, filed as application No. PCT/EP2009/063588 on Oct. 16, 2009, now Pat. No. 9,849,220.

(30) Foreign Application Priority Data

Oct. 16, 2008 (GB) .................................... 0818933

(51) Int. Cl.
*A61F 2/82* (2013.01)
*A61K 9/00* (2006.01)
(Continued)

(52) U.S. Cl.
CPC ............... *A61L 31/16* (2013.01); *A61L 31/10* (2013.01); *A61L 2300/406* (2013.01); *A61L 2300/608* (2013.01); *A61L 2420/08* (2013.01)

(58) Field of Classification Search
CPC .. A61F 2310/00389; A61F 2002/30576; A61F 2210/00; A61F 2230/0063;
(Continued)

(56) References Cited

U.S. PATENT DOCUMENTS

| 5,019,096 A | 5/1991 | Fox et al. |
| 5,624,411 A | 4/1997 | Tuch |

(Continued)

FOREIGN PATENT DOCUMENTS

| CN | 1925881 A | 3/2007 |
| CN | 101234201 A | 8/2008 |

(Continued)

OTHER PUBLICATIONS

Sanchez, E. et al.: "In vivo—in vitro study of biodegradable and osteointegrable gentamicin bone implants"; European J. of Pharmaceutics and Biopharmaceutics, Sep. 1, 2001, vol. 52(2), pp. 151-158. Elsevier Science Publishers B.V., Amsterdam , NL.

(Continued)

*Primary Examiner* — Ann Schillinger
(74) *Attorney, Agent, or Firm* — BakerHostetler

(57) ABSTRACT

An implantable medical device, which comprises a device substrate, a coating on the substrate which includes a drug, and a protective layer which overlies the coating. The protective layer comprises a polymer selected from the group consisting of polylactic acid, polyglycolic acid and a lactic acid/glycolic acid copolymer having a weight average molecular weight of not more than 40,000.

19 Claims, 4 Drawing Sheets

Figure 1:
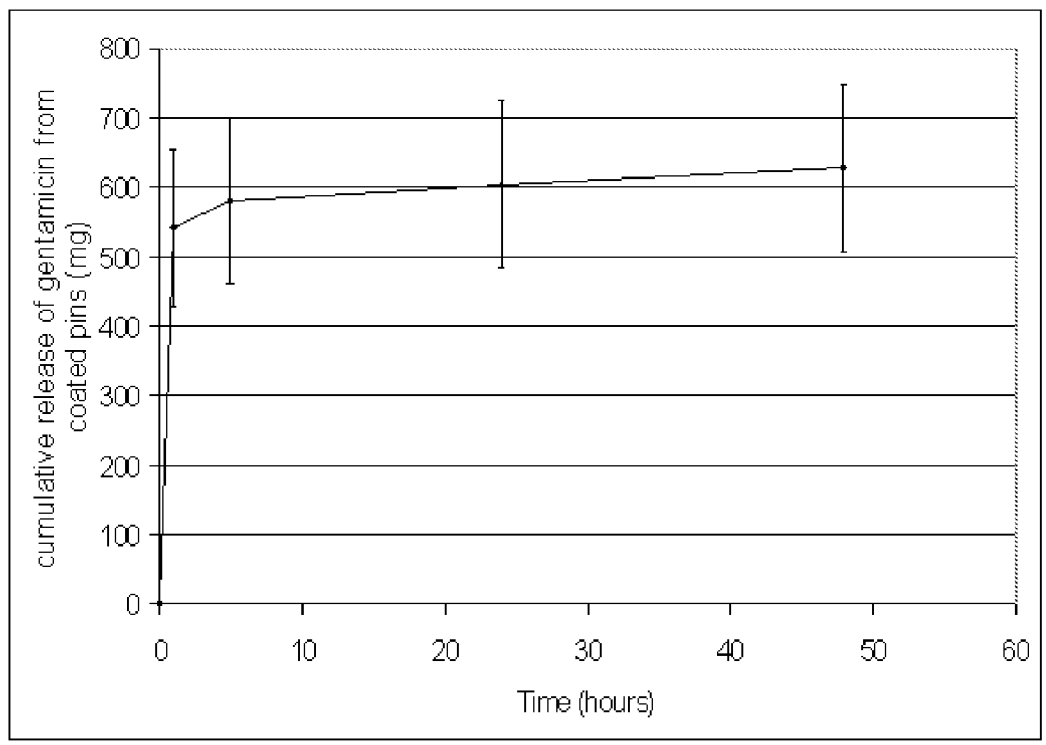

(51) Int. Cl.
*A61L 31/16* (2006.01)
*A61L 31/10* (2006.01)

(58) Field of Classification Search
CPC ........ A61F 2/0009; A61F 2/86; A61F 5/0036;
A61L 27/24; A61L 27/52; A61L 27/56;
A61L 27/54; A61L 27/06; A61L 27/227;
A61L 27/58; A61L 2300/406; A61L
2300/412; A61L 2300/414; A61L
2400/18; A61L 2420/00; A61L 2420/02;
A61L 2420/06; A61L 2420/08; A61L
31/16
See application file for complete search history.

(56) References Cited

U.S. PATENT DOCUMENTS

| | | | |
|---|---|---|---|
| 6,998,134 | B2 | 2/2006 | Schmidmaier et al. |
| 7,169,404 | B2 | 1/2007 | Hossainy et al. |
| 8,114,427 | B2 | 2/2012 | Schmidmaier et al. |
| 8,420,108 | B2 | 4/2013 | Kerr et al. |
| 9,849,220 | B2 * | 12/2017 | Li .................... A61L 31/16 |
| 2003/0083740 | A1 | 5/2003 | Pathak |
| 2004/0193255 | A1 * | 9/2004 | Shanley ............ A61F 2/91 |
| | | | 623/1.42 |
| 2004/0220656 | A1 | 11/2004 | Epstein et al. |
| 2005/0125054 | A1 * | 6/2005 | Bhat .................. A61L 27/54 |
| | | | 623/1.42 |
| 2006/0008504 | A1 | 1/2006 | Kerr et al. |
| 2007/0020312 | A1 | 1/2007 | Desnoyer et al. |
| 2007/0038289 | A1 * | 2/2007 | Nishide ............. A61F 2/91 |
| | | | 623/1.16 |
| 2007/0050010 | A1 * | 3/2007 | Bates ................. A61F 2/82 |
| | | | 623/1.15 |
| 2007/0141100 | A1 | 6/2007 | Sung et al. |
| 2007/0196423 | A1 | 8/2007 | Ruane et al. |
| 2007/0207184 | A1 | 9/2007 | Ruane et al. |
| 2007/0207189 | A1 | 9/2007 | Belcheva et al. |
| 2008/0038307 | A1 | 2/2008 | Hoffmann |
| 2008/0091277 | A1 | 4/2008 | Deusch et al. |

FOREIGN PATENT DOCUMENTS

| | | |
|---|---|---|
| EP | 0523926 A2 | 1/1993 |
| JP | 2008-502455 A | 1/2008 |
| JP | 2008-113827 A | 5/2008 |
| WO | 00/45744 A1 | 8/2000 |

OTHER PUBLICATIONS

Price, J.S. et al.: "Controlled release of antibiotics from coated orthopedic implants"; J. of Biomedical Materials Research, Jan. 1996, vol. 30(1), pp. 281-286. Wilev,New York, NY US.

Gollwitzer et al., "Antibacterial poly(D,L-lactic acid coating of medical implants using a biodegradable drug delivery technology", Journal of Antimicrobial Chemotherapy, vol. 51, 2003, 585-591.

Bari et al., "In vita-in characterization of gentamicin bone implants", Journal of Controlled Release vol. 83, 2002. pp. 352-364.

Aviv et al., "Gentamicin-Loaded Bioresorbable Films for Prevention of Bacterial Infections Associated with Orthopedic Implants", Journal of Biomedical Materials Research Part 1, Mar. 2007, 10 pages.

* cited by examiner

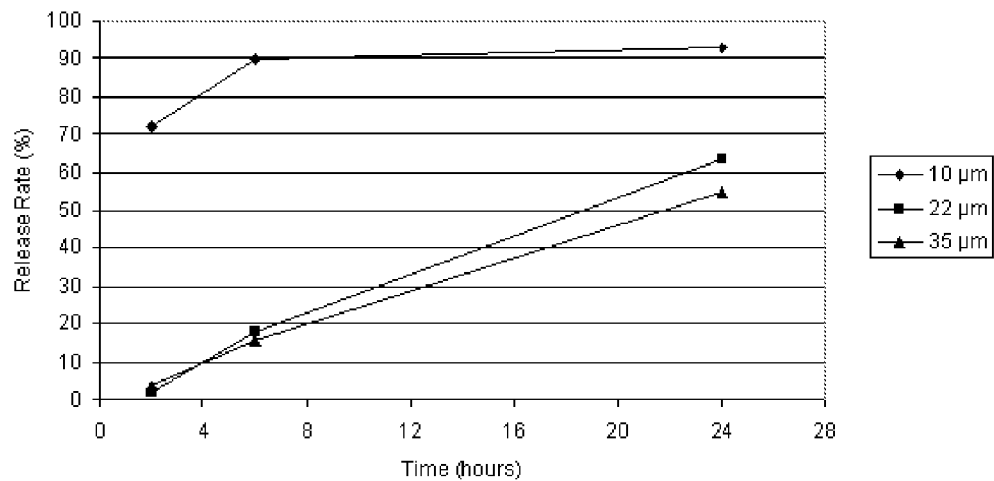
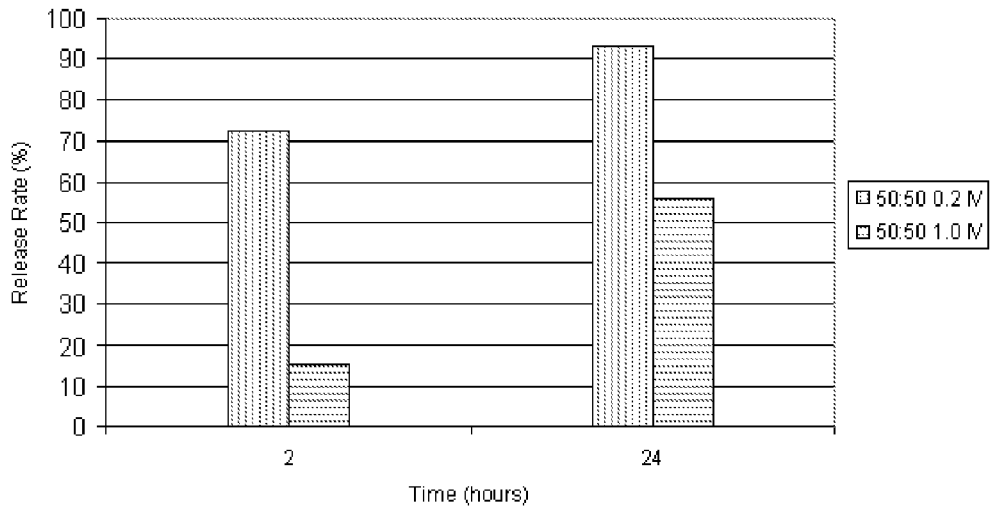

IMPLANTABLE MEDICAL DEVICE

CROSS-REFERENCE TO RELATED APPLICATIONS

This application is a continuation of U.S. application Ser. No. 13/124,532, filed on Jul. 27, 2011, which is a 371 national stage application of PCT/EP2009/63588, filed on Oct. 16, 2009, which claims the benefit of GB Appl. No. 0818933.4, filed on Oct. 16, 2008, the contents of each which are hereby incorporated in their entireties.

FIELD OF DISCLOSURE

This invention relates to an implantable medical device.

BACKGROUND OF THE INVENTION

It is desirable to control infection at the site of implantation of a medical device. In surgical procedures for the replacement of an orthopaedic joint, it is known to provide an antibiotic material within a bone cement composition.

It is known to provide an antibiotic material in a coating on the surface of a medical device. US-A-2007/0050010 discloses a vascular implant such as a stent having a coating which can contain a drug. A protective polymer layer can be provided on the coating to prevent degradation of the drug coating. The polymer can control the rate at which the drug in the coating is absorbed into the patient's bloodstream.

SUMMARY OF THE INVENTION

It can be desirable in order to minimise infection risk for an antibiotic in an implant coating layer to be released quickly after implantation.

The present invention provides an implantable medical device in which a drug coating layer has an overlying protective polymeric layer, in which the layer comprises polylactic acid, polyglycolic acid or a lactic acid/glycolic acid copolymer having a weight average molecular weight of not more than 40,000.

Accordingly, in one aspect, the invention provides an implantable medical device, which comprises:
a. a device substrate having a surface,
b. a coating on the surface of the substrate which includes a water soluble drug, and
c. a protective layer which overlies the coating, which comprises a polymer selected from the group consisting of polylactic acid, polyglycolic acid and a lactic acid/glycolic acid copolymer having a weight average molecular weight of not more than 40,000.

The device of the invention has the advantage that the protective layer can protect the coating prior to implantation of the device, for example during manufacture, transportation, pre-operative preparation, and delivery of the device to the implantation site. For example, it can restrict absorption of moisture by the drug which can then lead to a weakening of the physical structure of the coating (which can be a particular problem with coatings which contain highly deliquescent drug materials). The protective layer can protect the coating against abrasion, for example when the device is being manipulated and, in particular, during implantation when the device might contact surgical instruments or hard tissue (especially bone tissue). The protective layer can be displaced after the device has been implanted, allowing drug in the coating to be absorbed.

Displacement of the protective layer can involve degradation or dissolution or both as a result of contact with body fluids on implantation. Displacement of the protective layer can involve adsorption of body fluids so that the water content of the polymer matrix increases. The adsorbed water can allow migration through the protective layer of a hydrophilic drug. The adsorbed body fluids might cause some polymeric materials which might be used for the protective layer to swell. Adsorbed body fluids might be tightly bound within the protective layer, for example by hydrogen bonds, which might cause the layer to shrink slightly. Preferably, the protective layer dissolves so that underlying material (which can be the device substrate or the coating or another component) becomes exposed. This can be advantageous when an interaction (physical or chemical) is envisaged between a component of the device and natural tissue. For example, it can be desirable when osteoblast attachment is envisaged to form a bone-to-substrate connection. Dissolution of the protective layer can be relied on to expose the coating to body fluids so that the drug in the coating is absorbed. Swelling of the protective layer on initial exposure to body fluids can provide an initial mechanism for release of the drug from the coating, with subsequent release of the drug being facilitated by dissolution of the protective layer.

Preferably, the thickness of the protective layer is not more than about 20 μm, more preferably not more than about 15 μm, for example not more than about 10 μm. This has been found to allow release of drug quickly from the coating which underlies the protective layer.

Preferably, the thickness of the protective layer is at least about 3 μm, more preferably at least about 5 μm, for example at least about 8 μm. This has been found to provide suitable protection for the drug-containing coating. Preferably, the thickness of the protective layer is not more than about 40 μm, more preferably not more than about 30 μm, especially not more than about 20 μm, for example not more than about 15 μm or than about 12 μm. A preferred protective layer can have a thickness in the range 5 to 10 μm.

Preferably, the molecular weight of the polymer of the protective layer is at least about 10,000, more preferably at least about 15,000. This has been found to provide suitable protection for the drug-containing coating. Preferably, the molecular weight of the polymer of the protective layer is not more than about 30,000, more preferably not more than about 25,000, for example not more than about 20,000. This has been found to allow release of drug quickly from the coating which underlies the protective layer.

The viscosity average molecular weights of polymer materials are related to inherent viscosity by the Mark-Houwink equation:

$$IV = K M_v^a$$

where K and a are constants which have the values $5.45 \times 10^{-4}$ and 0.73 respectively for PLGA. The viscosity average molecular weight of a polymer will generally be close to the weight average molecular weight of that polymer if the spread of molecular weights is small.

The benefits provided by the present invention are particularly significant when the coating contains a drug which is highly soluble in aqueous media, especially to the extent that it is deliquescent. Such drugs can be particularly susceptible to degradation prior to implantation. Examples of suitable types of drugs include drugs having anti-inflammatory activity, bis-phosphonates (such as might be used in the treatment of osteoporotic conditions), drugs for pain relief, and growth factors.

Preferably, the drug is an antibiotic. A preferred group of antibiotics include amino-glycosides (or aminoglycans) such as amikacin, gentamicin, kanamycin, neomycin, netilmicin, streptomycin and tobramycin. Preferably, the drugs are present in the coating as the salt of the aminoglycoside with a strong acid. For example, a preferred drug is present as gentamicin sulphate. Preferably, the solubility of the drug is at least 40 $g \cdot l^{-1}$. The solubility is measured by making a saturated solution of the drug in de-ionised water at 25° C., and measuring the concentration of the solution using HPLC apparatus.

The solubility of the drug may be at least 50 $g \cdot l^{-1}$, preferably at least about 100 $g \cdot l^{-1}$, more preferably at least about 150 $g \cdot l^{-1}$, especially at least about 200 $g \cdot l^{-1}$, for example at least about 250 $g \cdot l^{-1}$, or at least about 350 $g \cdot l^{-1}$. Preferably, the drug is applied to the surface of the substrate in a solution, especially a solution in which the solvent is water based (for example including at least 80% by weight water, especially at least 95% water) in which its concentration is at least 50 $g \cdot l^{-1}$, preferably at least about 100 $g \cdot l^{-1}$, more preferably at least about 150 $g \cdot l^{-1}$, especially at least about 200 $g \cdot l^{-1}$, for example at least about 250 $g \cdot l^{-1}$, or at least about 350 $g \cdot l^{-1}$.

The coating can include more than one drug.

The coating can include additional materials which are provided to optimise properties of the coating, for example its physical properties, or to provide a desired tissue interaction when implanted. For example, the coating might include stabilising agents and excipients for the drug, for example radical scavenger and other antioxidant agents, agents to stabilise the drug against localised changes in pH, and desiccants.

The coating can preferably be applied as a solution, in which the solvent is then removed by use of one or more drying techniques. It will frequently be preferred for the solvent to include water. For example, when the applied coating consists essentially of gentamycin sulphate, the coating can be applied as a solution of the gentamycin sulphate in water. The concentration of the drug in the water should preferably be high to help to minimise subsequent drying times. For example, the concentration of gentamicin in water might be in the range 200 to 400 $mg \cdot ml^{-1}$.

The device can be subjected to a heating step. This is particularly preferred when the polymer used in the protective layer is thermoplastic. A heating step can be performed after application of a coating in solution and removal of solvent from the protective layer. It can help to eliminate discontinuities in the protective layer so that the underlying drug coating is better protected prior to implantation of the device. The heating step can help to control the rate at which the drug is released from the surface of the device, for example by inhibiting quick release through discontinuities or other imperfections or inconsistencies in the protective layer.

It can be preferable to conduct the heating step under vacuum, for example to minimise oxidation of the materials of the layers. The heating temperature will depend on the softening point of the polymer. The heating step should cause the polymer to soften so that it can flow. The flow of the polymer should be sufficient to allow discontinuities in the protective layer to close. The polymer need not flow freely. Factors affecting the heating conditions might include the polymer of the protective layer, its molecular weight, the thermal mass of the device substrate, and the thickness of the protective layer. Suitable heating conditions for a 50:50 PLGA might involve exposure to a temperature of from 85° C. to 110° C. for 90 minutes under vacuum.

The substrate can be mounted in a fixturing device during the application of the drug coating. The fixturing device can be configured to rotate or otherwise move the substrate in a predetermined way under the coating nozzle to provide a uniform coating over all of the relevant surface of the substrate.

The solvent for the coating can be removed by techniques such as the application of heat, exposure to an air stream, and so on. A preferred drying technique can involve exposure to radiation from an infrared source, while positioned in an airstream. When the coating is applied as a solution, it can be applied by a spray technique, in which the solution is atomised and then driven towards the substrate using a stream of an inert gas (for example nitrogen, argon or helium). The solution should be filtered before it is sprayed to remove particulate impurities. Such techniques are known.

The coating can be applied directly to the surface of the substrate. The coating can be applied to an intermediate layer which is provided on the substrate. For example, it might be preferred for some applications to provide a sealing layer on a substrate, for example when the substrate comprises a material which gives rise to an adverse tissue reaction when the device is implanted. Such an intermediate layer might be provided by a polymer which is inert towards materials with which it comes into contact when the device is implanted.

Preferably, the drug is present on the substrate in a dosage of at least about 50 micrograms for each square centimetre of the substrate (referring to the gross area of the substrate, irrespective of any pores or other surface features on or in the surface of the substrate), preferably at least about 100 $\mu g \cdot cm^{-2}$. Preferably, the drug is present on the substrate in a dosage of at least about 200 $\mu g \cdot cm^{-2}$, more preferably at least about 300 $\mu g \cdot cm^{-2}$, for example at least about 400 $\mu g \cdot cm^{-2}$ or at least about 800 $\mu g \cdot cm^{-2}$. Preferably, the drug is present on the substrate in a dosage of not more than about 2000 $\mu g \cdot cm^{-2}$, more preferably not more than about 1500 $\mu g \cdot cm^{-2}$, especially not more than about 1000 $\mu g \cdot cm^{-2}$, for example not more than about 500 $\mu g \cdot cm^{-2}$, or not more than about 300 $\mu g \cdot cm^{-2}$.

It will generally be preferred that the drug coating does not include diluents or other inert agents. It might be that the drug coating might include other active agents which promote a beneficial reaction in the patient. For example, the drug coating might include an agent which can promote growth of bone tissue.

Preferably, the thickness of the coating is not more than about 10 μm, more preferably not more than about 7 μm, for example not more than about 5 μm.

Preferably, the thickness of the coating is at least about 1 μm, more preferably at least about 2 μm, for example about 3 μm. This has been found to provide suitable protection for the drug-containing coating When the surface region of the device substrate is porous, which can be for the purpose of accommodating ingrowth of bone tissue, the measured thicknesses of the coating and of the protective layer are to be considered in relation to the surfaces which are defined by the detailed structure of the substrate.

The protective layer can be formed from polymers of lactic acid or glycolic acid or both. Preferably, the layer is formed from a lactic acid/glycolic acid copolymer. The acids might be present in the polymer in the form of their esters and/or salts of the acids. For example, it can be preferred to introduce the ester end groups to cap the polymerised acid, for example as a result of reaction with acetic anhydride.

Preferably, the polymer is selected so that it is amorphous rather than crystalline. It can be preferred that the lactic acid in the copolymer is in the form of the d,l-lactide and that it is amorphous. The amount of glycolide in the copolymer should be maintained sufficiently low to ensure that the copolymer does not incorporate blocks of glycolide monomer which introduce crystalline regions into the polymer. Use of an amorphous polymer has the advantage of easier processing using melt processing techniques, or using solvent processing techniques, or using a combination of the two.

The copolymer of lactic and glycolic acids can be represented by the formula:

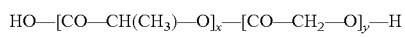

Preferably the copolymer is a random copolymer and does not have a significant blocks of one of the monomer components. A suitable copolymer can be formed from lactic acid and glycolic acid in which the ratio (molar) of x:y is at least about 30:70, preferably at least about 40:60, especially at least about 45:55. Preferably, the ratio is not more than about 70:30, more preferably not more than about 60:40, especially not more than about 55:45, for example about 50:50. Such polymers have been found to provide significant benefits in terms of protection for the drug-containing coating prior to implantation and then minimal resistance to dissolution of the drug after implantation, through swelling of the material of the protective layer and then dissolution. These polymers can have the advantage of processability using melt processing and/or solvent processing techniques, especially if they are amorphous. Preferably, the glycolide content in the copolymer is maintained sufficiently high to ensure that the copolymer can be degraded sufficiently quickly after implantation.

An example of a preferred lactic acid/glycolic acid copolymer is that sold under the trade mark PURASORB PDLG5002 by Purac of Gorinchem, Netherlands. This material has a weight average molecular weight of about 17,500 (it being understood that a suitable polymer for the protective layer will have a range of molecular weights distributed about a peak distribution).

The protective layer can include additional materials which are provided to optimise properties of the protective layer, for example its physical properties, or to provide a desired tissue interaction when implanted. For example, the protective layer might include radical scavenger and other antioxidant agents, agents to stabilise the drug against localised changes in pH, and desiccants.

The protective layer can preferably be applied as a solution, in which the solvent is then removed by use of one or more drying techniques. It will frequently be preferred for the solvent to include one or more organic solvents. Suitable solvents might include, for example, acetone, ethyl acetate, chloroform, and methylene chloride. For example, when the applied coating consists essentially of lactic acid/glycolic acid copolymer, the solvent can be acetone. Preferably, the polymer is present in the solution in a concentrating of at least about 0.1% w/w, more preferably at least about 1.0%, especially at least about 5%. The polymer might be present in the solution in a concentration of not more than about 20% w/w, preferably not more than about 15%, for example about 10%. The objective is to achieve the optimum thickness of polymer for the performance of the protective layer. When a more dilute polymer solution is used, longer spray times can be required to achieve the specified thickness of the protective layer. This thickness is optimum for the performance of the protective layer. If more dilute polymer solutions are used then longer application times will be required to achieve the specified thickness of the protective layer.

The protective polymer layer can be deposited on to the substrate using electrostatic coating processes. Use of an electrostatic process can help to provide a uniformly thin polymer layer that conforms to the surface features of the substrate. This technology prevents the masking of the features and the high conformal nature of the protective layer results in coverage with minimal decrease in surface area of the substrate implant. The morphology of the coating is affected by the flow rate of the solution into the nozzle. For uniformly thin, film-like, and conformal layers, lower flow rates can be preferred (for example 1 to 4 ml·h$^{-1}$). Voltage, distance between the nozzle and the substrate, and length of time of coating also require controlled and specified values for optimal morphology of the protective layer. During electrostatic process the substrate is required to be grounded to attract the charged coating particles. For a complex geometry like a hip stem this might require a specialised fixture. The complexity of the fixturing device can be increased further if masking of areas not to be coated is required. The fixturing device can be configured to rotate or otherwise move the substrate in a predetermined way under the coating nozzle to provide a uniform coating over all of the relevant surface of the substrate.

The solvent for the protective layer can be removed by techniques such as the application of heat, exposure to an air stream and so on. A preferred drying technique can involve exposure to hot air in an oven. When the coating is applied as a solution, it can be applied by a spray technique, in which the solution is atomised and then driven towards the substrate using a stream of an inert gas (for example nitrogen, argon or helium). The solution should be filtered before it is sprayed to remove particulate impurities. The application of charge to the droplets of the solution can be preferred to facilitate controlled application of the coating. Such techniques are known.

Preferably the area of the device substrate which is covered by the drug coating is less than the area which is covered by the protective layer, so that the protective layer extends beyond the area covered by the drug coating on to the surface of the device substrate beyond the drug coating. This has the advantage that the protective layer can be sealed directly on to the surface of the device substrate to inhibit ingress of body fluids at the edge of the drug coating.

The device of the invention can be a component of an orthopaedic implant, for example a component of a joint prosthesis, a component such as a nail or a bone plate for use in treatment of bone fractures and other traumas, a fixation component such as a bone screw or pin, and a spinal implant device. For example, the device might be a component of a hip joint prosthesis or a knee joint prosthesis or an elbow joint prosthesis or a shoulder joint prosthesis or a finger joint prosthesis or an ankle joint prosthesis. The surface of the substrate on which the coating is provided is provided at least in part by a metal, for example a stainless steel or a cobalt chromium molybdenum alloy or a titanium alloy. Such materials are known for use in the manufacture of orthopaedic joint prosthesis components. The surface of the substrate can have applied to it a layer of a material which promotes favourable reaction when the device is implanted, for example to promote ingrowth of bone tissue into the surface of the substrate to secure the device in a bone cavity. For example, the device might have applied to it a layer of a ceramic material such as a hydroxy apatite material.

The surface of the component on which the coating is provided might be polished. The surface might be roughened for example by sand blasting. The surface might have pores formed in it, for example as a result of the application to it of sintered metal beads as in components which are available from DePuy Orthopaedics Inc under the trade mark Porocoat, or in the form of an open cell structure in the manner of a foam.

The device substrate surface can contain features to facilitate bone in-growth and the coating should not mask these surface features. It is desirable to achieve an accurate, reproducible, and uniform dose of the drug across the surface of the substrate. For these reasons, it can be desirable to use a spray coated with precise control over droplet size. For most conventional spray atomizers, the propellant pressure is the parameter that controls droplet size and therefore care must given in the selection of the appropriate propellant pressure parameter in achieving the optimal dose. Since it is important to achieve a high degree of reproducibility of dose of drug deposited a spraycoater that can spray nano-droplets has been found to be useful. The amount of drug that is deposited on to the surface is determined by the length of time that the drug is sprayed onto the substrate surface. The longer the spray time the larger the amount of drug deposited on to the surface of the substrate. To achieve a high level of accuracy longer spray times are more desired rather than an increased number of spray cycles. If the substrate becomes too wet during the coating application it is possible to dry mid-cycle with the application of infra-red heat lamps. The coating/drying steps can be alternated until the appropriate dose of drug is achieved. The drug coating can be dried prior to the deposition of the polymer layer. Drying can be accomplished by air-drying or drying in a vacuum or conventional heated oven.

In another aspect, the invention provides a method of making an implantable medical device which comprises applying a coating which includes a water soluble drug to the surface of the device, and applying a protective layer over the coating, which comprises a polymer selected from the group consisting of polylactic acid, polyglycolic acid and a lactic acid/glycolic acid copolymer having a weight average molecular weight of not more than 40,000. Features of the device which is made by this method are discussed above in relation to the device aspect of the invention.

The device of the invention can be used in a method of surgery in which the device is implanted in a patient, where the device is exposed to body fluids which cause the drug in the coating to be released from the surface of the substrate, in particular to expose the patient to the drug in a burst release. Preferably, at least 90% of the drug is released from the surface of the substrate within a period of not more than 7 days, more preferably not more than about 5 days, especially not more than about 2 days, particularly not more than about 1 day. It can be preferred that at least 90% of the drug is released from the surface of the substrate within a period of not more than about 16 hours, more preferably not more than about 12 hours, especially not more than about 8 hours, for example not more than 4 hours. It can be preferred that at least 60% of the drug is released from the surface of the substrate within a period of not more than about 10 hours, more preferably not more than about 7 hours, especially not more than about 4 hours, for example not more than about 3 hours.

BRIEF DESCRIPTION OF THE DRAWINGS

The invention is described below by way of example, with reference to the accompanying drawings, in which:

FIG. 1 shows the amount of gentamicin sulphate that is released from coated titanium pins.

FIG. 2 shows the result of a zone of inhibition test on a grit-blasted titanium coupon coated with one-step coating of gentamicin sulphate and PLGA 50/50, challenged with staph epidermis.

FIG. 3*a* is an SEM image of the surface of an uncoated grit-blasted titanium surface.

FIG. 3*b* is an SEM image of the surface of a grit-blasted titanium coupon with gentamicin and PLGA coating. This coupon has not been subjected to a heating step. It can be seen that the exposed surface of the protective polymer layer is uneven, with the thickness of the layer being greater in some areas than in others.

FIGS. 4*a-c* shows SEM images of the surface of grit-blasted titanium coupons which were coated, incubated in PBS for 24 hours, rinsed and dried. The coupon in FIG. 4*a* was coated with gentamicin/PLGA using the two-step coating method and no polymer underlayer. The coupon in FIG. 4*b* was undercoated with a 30 second spray of PLGA before coating using two-step process. The coupon in FIG. 4*c* was undercoated with a 60 second spray of PLGA before coating using two step process.

FIG. 5 illustrates the effect on drug release rate of a variation in the thickness of the protective polymer layer.

FIG. 6 illustrates the effect on drug release rate of a variation in the molecular weight of the polymer of the protective layer.

DETAILED DESCRIPTION OF THE INVENTION

EXAMPLES

Example 1

The antibiotic coating and the protective layer are applied in two steps. By using a two-step method of coating it is possible to deposit a high dose of gentamicin but minimal amounts of polymer. Minimising the amount of polymer that could serve as a barrier between the surface of the implant and the newly-formed bone is extremely important in the optimal fixation of the polymer.

The first step of the two-step method is the deposition of gentamicin. Here, the gentamicin is dissolved in water at a high concentration (e.g. 200 to 400 $mg \cdot ml^{-1}$). The solution is filtered using a filter of appropriate size (for example about 2.7 μm) to remove insoluble impurities. This solution is transferred to the reservoir of an atomisation nozzle (such as that which is sold under the trade mark Tridek). An air source (or an inert gas such as nitrogen, argon, helium) as propellant is connected by tubing to the nozzle. The propellant is used to break up the fluid jet into droplets. The device to be coated can be stationary or fixtured to a rotating fixturing device.

The reservoir pressure is set to 34.5 kPa (5 psi) and the nozzle pressure is set to 551.6 kPa (80 psi), and the distance between the nozzle and the substrate is set at 16 to 18 cm. The substrate is sprayed with the solution for 4 seconds. The substrate is air dried until it appears dry. The coating and drying cycle is repeated three times to achieve a target dose of drug on the substrate of 1 $mg \cdot cm^{-2}$.

The drug coated substrate is then coated with a copolymer of lactide and glycolide, which are present in the polymer in a mole ratio of 50:50. The copolymer was supplied by Purac. The polymer was dissolved in acetone to a concentration of 10% w/w.

Once the gentamicin layer is finished the substrate can now be coated with a poly(lactide co-glycolide) layer. The purpose of the polymer layer is to prevent any loss of the gentamicin coating during shipping, handling, insertion, etc. A solution of the polymer is prepared by dissolving the polymer pellets in acetone to a concentration of 10% w/w. The distance between the nozzle and the substrate is about 6 to 7 cm and the flow rate is 4 ml·hour$^{-1}$. The substrate is grounded, and a potential difference is maintained between the nozzle and the substrate of about 9 to 12 kV. Spraying is continued for 60 seconds.

Following polymer deposition further drying might be required in a drying oven. Subsequent to drying the coated device would be packaged shipped to sterilization facility. Sterilization would be accomplished by an appropriate method for orthopaedic devices.

Example 2

A set of titanium coupons, each having a surface area of 5 cm$^2$, were initially coated with gentamicin sulphate to the target dose of 1 mg·cm$^{-2}$. A subset of the coupons were randomly selected from these gentamicin coated samples for coating with the PLGA topcoat. The coated coupons were sterilised using gamma radiation.

Analysis of elution rate of gentamicin in de-ionised water from the two types of coupons indicated a significantly larger amount of gentamicin sulphate was present on coupons that contained the protective top layer relative to those with no polymer top coat. For example, the total amount of gentamicin sulphate that eluted from two sets of coupons containing a topcoat was 4.9 and 6.9 mg, respectively. However, the total amount of gentamicin sulphate that eluted from coupons without the topcoat was only 3.3 and 3.6 mg, respectively. Analysis of the coupon surface after elution using FTIR and XPS indicated that no gentamicin sulphate remained after elution on the surface of the coupons. This data suggests the importance of the presence of the polymer topcoat. Coupons containing only the gentamicin coating can be envisioned as a donut with powdered sugar coating that can be shaken off during shipping and handling. The addition of the polymer topcoat fixes the gentamicin on to the surface of the coupon.

Although many of the experiments that we have conducted on coated substrates have a concentration of gentamicin sulphate of 1 mg·cm$^{-2}$, this coating system is highly flexible providing doses as low as 0.01 mg·cm$^2$ and doses that can exceed the mg·cm$^{-2}$ target.

Providing the high dose of gentamicin sulphate in a discrete layer rather than dispersed within a polymer matrix results in a rapid burst release of the gentamicin. Ninety percent of the gentamicin sulphate is released within the first 24 hours after immersion into physiological media and another ten percent is released by 48 to 72 hours (see FIG. 1).

In contrast, the release rate and bioefficacy of gentamicin sulphate was tested from coupons coated using a one-step coating where the gentamicin sulphate and the polymer are deposited together on the surface. Due to the incompatibility of gentamicin sulphate and PLGA only small concentrations of gentamicin can be made miscible with PLGA/organic solutions (ratio of gentamicin sulphate to PLGA is 1:10). Due to the inequality in ratio of drug to polymer a significant amount of polymer is deposited in order to achieve the target dose of gentamicin sulphate. This large polymer concentration results in a slow rate of release of the gentamicin sulphate, resulting in concentrations that are below the MIC. This is demonstrated during bioefficacy testing of the coupons in a zone of inhibition test.

Figure 2:
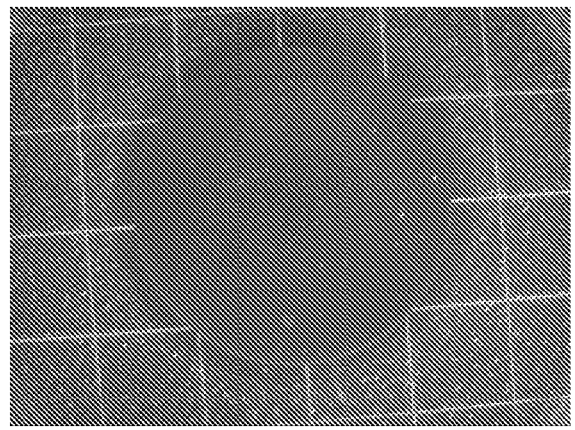

Within the first 24 hours of the test the release rate of gentamicin is so low that the bacteria can actually grow upon the surface of the coupon (FIG. 2).

Figure 3A:
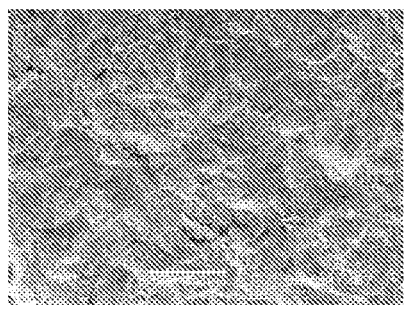
Figure 3B:
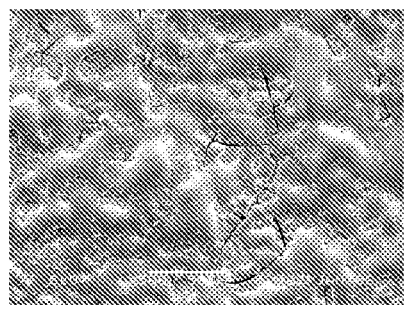
Figure 4A:
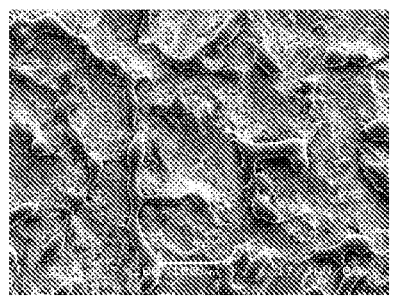
Figure 4B:
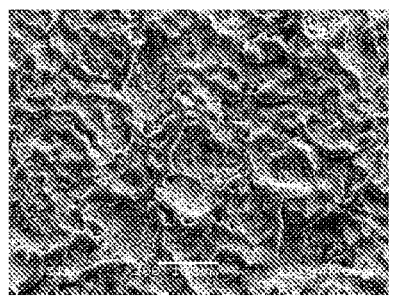
Figure 4C:
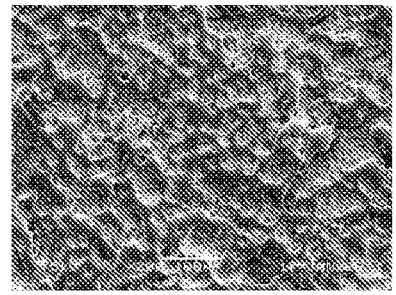

Another advantage of this two layer approach to the coating is that the polymer disappears quickly. This allows large areas of the specially engineered surface features to be exposed and available for osteoblast attachment. The length of time to achieve this virtually uncoated surface was tested. Titanium grit-blasted coupons were coated with gentamicin (1 mg·cm$^{-2}$) and top-coated with PLGA. The coupons were incubated in PBS overnight, rinsed and dried. After drying the surface of coupons was analysed with SEM. Over the 24 hours of incubation much of the coating was lost and large areas of the surface of the coupon were exposed. Data relating to the loss of the coating and exposure of the coupon surface are set out in FIGS. 3$a$-$b$ and 4$a$-$c$. Two other sets of coupons were prepared, one was first sprayed with low molecular weight PLGA for 30 seconds before applying the two-layer coat, the other was sprayed for 60 seconds before applying the two layer coat. Both sets of coupons were incubated in PBS, rinsed and dried as described above. SEM analysis indicates that increasing the amount of polymer that contacts the titanium surface results in much greater retention of the coating on the titanium surface after incubation (see FIGS. 4$a$-$c$).

FTIR and XPS data confirm that no gentamicin remains on the surface following incubation and the patches of coating that remain on the surface are composed only of PLGA. Areas without patches were also analysed by FTIR and XPS and found to be titanium.

The effect of the coating on osteoblasts was tested in vitro by plating MG63 (human osteosarcoma) cells on to the surface of uncoated titanium coupons, titanium coupons coated with polymer, and titanium coupons coated with the two step system. At specific time points the coupons were removed fixed and stained using Live/Dead assay. Samples were analysed using a confocal microscope. No significant difference in numbers of live cells was apparent between the uncoated, and two step system during the three days that the cells were tested.

Example 3

The 2.54 cm diameter titanium coupons with a grit-blast finish were sonicated in isopropyl alcohol in a Branson ultrasonic bath for 60 minutes, then rinsed three times with de-ionised water and dried in an oven under 100° C. Coupons were weighed and recorded after drying. The rim area of the coupons were then masked using 1.9 cm O-rings with metal coupon holders.

Gentamicin sulphate was dissolved in purified water to a concentration of 400 mg·ml$^{-1}$ and filtered through a 2.7 μm nylon syringe filter. The gentamicin solution was sprayed using a spray nozzle (as sold under the trade mark EFD 481). The processing parameters were:

Needle stroke setting 4.9;
Spray distance 17.78 cm;
Propellant pressure 103 kPa (15 psi);
Reservoir pressure 20.7 kPa (3 psi).

The spray cycle was 4 seconds for 4 times with 60 second intervals. The coupons were air dried for 60 minutes then stored in a nitrogen box overnight. Coupons were unmasked then weighed for obtaining the gentamicin sulphate coating weights.

A 50:50 PLGA, 0.20 IV polymer (estimated viscosity average molecular weight 16,500) was dissolved in acetone to a concentration of 100 mg·ml$^{-1}$. The solution was sprayed using an electrostatic nozzle (as sold under the trade mark Terronics Dart) with small setback on to the gentamicin-coated coupons. The processing parameters were:

Spray distance 6.5 cm;
Flow rate 4 ml·h$^{-1}$,
Voltage 9 kV.

Spray time was set for desired thickness. For example, 90 and 180-second were set to obtain 5.8 and 11.6 mg coating weights that yielded about 5 and 10 μm thickness respectively on each coupon.

Additional samples were made using other materials, as follows.

75:25 PLGA 0.73 IV (estimated viscosity average molecular weight 126,000),

75:25 PLGA 0.23 IV (estimated viscosity average molecular weight 19,000),

50:50 PLGA, 1.0 IV (estimated viscosity average molecular weight 200,000).

These materials were applied using a solution having a concentration, 20 mg·ml$^{-1}$. The flow rate and spray time were adjusted accordingly to obtain the desired drug dose on the substrate surface.

The coupons were exposed to heat under vacuum in an oven. The sample made using 50:50 PLGA 0.2 IV for the protective layer was exposed to a temperature of 85° C. for 90 minutes. The samples made using the other protective layer materials were exposed to a temperature of 110° C. for 90 minutes. A comparison between the coupons before and after the heating step showed that the protective layer changed from a pre-heating state in which its thickness is variable, with regions in which the layer was undesirably thin and other regions in which the layer was undesirably thick, and yet other regions in which the drug coating was exposed, to a post-heating state in which it is continuous with a generally uniform thickness across the surface of the device.

Example 4

The thickness of the polymer topcoat was calculated using coated polymer weight, the polymer density, and the coating area adjusted by the surface area indices (SAI), measured using an optical profiler (as sold under the trade mark Veeco Wyko NT9100) of both the gentamicin drug coating and the polymer protective layer.

The coupons which were coated with 50:50 PLGA 0.2 IV, prepared by the process of Example 3, were individually placed in suitable polypropylene containers with the protective polymer layer facing upwards. 25 ml de-ionised water was supplied to each of the containers. The containers were placed into a oven, pre-heated to 37° C. The containers were taken out at the desired time points. An aliquot of the elution media was transferred to auto sampler vials for HPLC-CAD analysis. The gentamicin contents in the elution media were obtained by HPLC-CAD. The release percentages of the coupons were calculated via original weight of the coated gentamicin with the adjustment of the pre-determined moisture and potency.

The gentamicin release rates were calculated over the time periods of 2 hours, 6 hours, 24 hours and 72 hours. It was found that increasing the thickness of the protective layer results in a slower release rate. It was found that increasing the molecular weight of the polymer of the protective layer results in a slower release rate.

Example 5

The samples under elution study were taken out from the elution media at the desired time points. The dried samples were sputter coated with a thin layer of gold. The SEM analysis was performed using a scanning electron microscope (JEOL JSM-5900LV). Three separate regions approximately 30 mm$^2$ were evaluated across the surface of the coupon. The images were captured using the standard SEM secondary electron image (SEI) detector and the back scattered electron image (BEI) detector. The BEI images clearly show exposed regions of the coupon surface as white dots in contrast to the darker polymer background. The proportion of remaining polymer was analysed using three BEI images for each coupon sample using Image Pro 6.2 software from MediaCybernetics.

The gradual erosion of the 50:50 PLGA 0.2 IV thin layer coating has occurred from the coupon surface over the course of the 7 day elution study. The analysis indicated a 99.0% polymer area for the 2 hour elution sample in contrast with a 93.1% polymer area for the 7 day sample.

The effects of thickness, PLGA molecular weight, and polymer composition after exposure to the elution solution for 7 days are illustrated in FIG. 6. The thin coating of 50/50 PLGA 0.2 IV material degraded more quickly than others. The thicker coating with the same materials retained more polymer coverage. The coating layer of the 50/50 PLGA 1.05 IV appeared to be intact after 7 days. The 75/25 PLGA with the same low IV but with higher L/G ratio also showed slower degradation.

What is claimed is:

1. An implantable medical device comprising:
   an orthopedic device substrate having a surface;
   a coating on at least a portion of the surface of the substrate, the coating having a thickness of about less than 10 μm, the coating comprising a water soluble antibiotic drug; and,
   a protective layer disposed over the coating, the protective layer comprising a biodegradable polymer that is polylactic acid or a lactic acid copolymer and having a weight average molecular weight of not more than 40,000 g/mol;
   wherein the device is configured to provide an initial burst release of at least 60% of the antibiotic drug within 10 hours of implantation and at least 90% of the antibiotic drug within 1 week;
   wherein the device is configured to contact bone; and,
   wherein the device is configured to control infection at an orthopedic surgical site.

2. The device of claim 1, wherein the device is configured to provide a release at least 90% of the drug within 1 day.

3. The device of claim 1, wherein the device is configured to provide an initial burst release of at least 60% of the drug within 3 hours.

4. The device of claim 1, wherein the weight average molecular weight of the polymer is less than 20,000 g/mol.

5. The device of claim 1, wherein the surface of the substrate on which the coating is provided is at least in part a metal.

6. The device of claim 1, wherein the surface of the substrate on which the coating is provided includes one or more pores.

7. The device of claim 1, wherein the coating has a thickness of about less than 7 μm.

8. The device of claim 1, wherein the coating has a thickness of about less than 5 μm.

9. The device of claim 1, wherein the coating has a thickness in the range of about 1 μm to about 5 μm.

10. The device of claim 1, wherein the thickness of the protective layer is not more than about 20 μm.

11. The device of claim 1, wherein the thickness of the protective layer is not more than about 10 μm.

12. The device of claim 1, wherein the protective layer has a thickness in the range of about 5 μm to about 10 μm.

13. The device of claim 1, wherein the protective layer is configured to swell upon exposure to body fluid so as to provide an initial mechanism of the initial burst release of the antibiotic drug from the coating, and wherein the protective layer is configured to dissolve after swelling so as to provide a subsequent mechanism of release of the antibiotic drug from the coating.

14. The device of claim 1, wherein the weight average molecular weight of the polymer is in the range of at least about 10,000 g/mol to less than about 30,000 g/mol.

15. The device of claim 1, wherein the water soluble antibiotic drug is present on the surface of the substrate in a dosage of not more than about 2000 $\mu g \cdot cm^{-2}$.

16. The device of claim 1, wherein the water soluble antibiotic drug is present on the surface of the substrate in a dosage of not more than about 1000 $\mu g \cdot cm^{-2}$.

17. The device of claim 1, wherein the water soluble antibiotic drug is present on the surface of the substrate in a dosage range of at least about 50 $\mu g \cdot cm^{-2}$ to not more than about 1000 $\mu g \cdot cm^{-2}$.

18. The device of claim 1, wherein the water soluble antibiotic drug is present on the surface of the substrate in a dosage range of at least about 100 $\mu g \cdot cm^{-2}$ to not more than about 500 $\mu g \cdot cm^{-2}$.

19. The device of claim 1, wherein the water soluble antibiotic drug is present on the surface of the substrate in a dosage range of at least about 200 $\mu g \cdot cm^{-2}$ to not more than about 500 $\mu g \cdot cm^{-2}$.

* * * * *